(12) United States Patent
Ritter

(10) Patent No.: US 11,484,635 B2
(45) Date of Patent: Nov. 1, 2022

(54) DISPLAY APPARATUS OF A MEDICAL TREATMENT DEVICE

(71) Applicant: B. Braun Avitum AG, Melsungen (DE)

(72) Inventor: Kai-Uwe Ritter, Melsung (DE)

(73) Assignee: B. Braun Avitum AG, Melsungen (DE)

( * ) Notice: Subject to any disclaimer, the term of this patent is extended or adjusted under 35 U.S.C. 154(b) by 0 days.

(21) Appl. No.: 17/274,255

(22) PCT Filed: Sep. 6, 2019

(86) PCT No.: PCT/EP2019/073861
§ 371 (c)(1),
(2) Date: Mar. 8, 2021

(87) PCT Pub. No.: WO2020/053097
PCT Pub. Date: Mar. 19, 2020

(65) Prior Publication Data
US 2021/0353839 A1  Nov. 18, 2021

(30) Foreign Application Priority Data

Sep. 10, 2018  (DE) ..................... 10 2018 122 035.9

(51) Int. Cl.
*A61M 1/16* (2006.01)
*G06F 3/14* (2006.01)
(Continued)

(52) U.S. Cl.
CPC ......... *A61M 1/1601* (2014.02); *G06F 3/1454* (2013.01); *G09G 5/14* (2013.01);
(Continued)

(58) Field of Classification Search
CPC .......... A61M 1/1601; A61M 2205/505; G09G 5/38; G09G 5/14; G09G 2340/0442; G09G 2380/08; G06F 3/1454
See application file for complete search history.

(56) References Cited

U.S. PATENT DOCUMENTS

| | | | |
|---|---|---|---|
| 7,038,588 B2 * | 5/2006 | Boone | A61G 12/00 340/573.1 |
| 2003/0018395 A1 * | 1/2003 | Crnkovich | G05B 15/02 700/11 |

(Continued)

FOREIGN PATENT DOCUMENTS

KR    2010-0008684 A  *  1/2010  ............. H04H 20/71

OTHER PUBLICATIONS

"Dialog+ Dialysis Machine," retrieved from the Internet: https://www.bbraunusa.com/content/dam/b-braun/us/website/products-and-therepies/renal-therapies/clinical-support/dialog-v9-1x-ifu.pdf.bb-.bb-.50982881/dialog-v9-1x-ifu.pdf, May 31, 2016, 284 pages.

(Continued)

*Primary Examiner* — Jennifer Mehmood
*Assistant Examiner* — Donna J. Ricks
(74) *Attorney, Agent, or Firm* — Christopher A. Rothe; Culhane Meadows, PLLC

(57) ABSTRACT

A display device of a dialysis machine for displaying various parameters containing a quantity of patient-related treatment parameters and a quantity of clinic-related CIS parameters. The display device has one display and an input unit to individually modify the quantity of patient-related treatment parameters or the quantity of clinic-related CIS parameters. The display includes a display area divided into a first display panel and a second display panel. The display can be switched to a treatment configuration in which the quantity (Continued)

of patient-related treatment parameters is displayed exclusively in the first display panel and the quantity of clinic-related CIS parameters is displayed exclusively in the second display panel. The display can also be switched to a CIS configuration in which the quantity of patient-related treatment parameters is displayed exclusively in the second display panel and the quantity of clinic-related CIS parameters is displayed exclusively in the first display panel.

15 Claims, 3 Drawing Sheets

(51) Int. Cl.
*G09G 5/14* (2006.01)
*G09G 5/38* (2006.01)

(52) U.S. Cl.
CPC ......... *G09G 5/38* (2013.01); *A61M 2205/505* (2013.01); *G09G 2340/0442* (2013.01); *G09G 2380/08* (2013.01)

(56) References Cited

U.S. PATENT DOCUMENTS

| | | | |
|---|---|---|---|
| 2005/0093886 A1* | 5/2005 | Kubota | H04N 1/3872 |
| | | | 345/619 |
| 2006/0146059 A1 | 7/2006 | Inoue et al. | |
| 2009/0099871 A1* | 4/2009 | Gadodia | G06Q 10/06 |
| | | | 705/3 |
| 2013/0317850 A1 | 11/2013 | Bene et al. | |
| 2016/0239203 A1* | 8/2016 | Sato | G06F 3/04883 |
| 2017/0017764 A1 | 1/2017 | Tsugo | |
| 2019/0110100 A1* | 4/2019 | Gao | H04N 21/4858 |
| 2020/0201545 A1* | 6/2020 | Li | G06F 9/451 |

OTHER PUBLICATIONS

German Search Report received in Application No. 10 2018 122 035.9 dated May 17, 2019, 18 pages.
International Search Report received in Application No. PCT/EP2019/073861 dated Dec. 12, 2019, 5 pages.
Written Opinion received in Application No. PCT/EP2019/073861 dated Dec. 12, 2019, 20 pages.

* cited by examiner

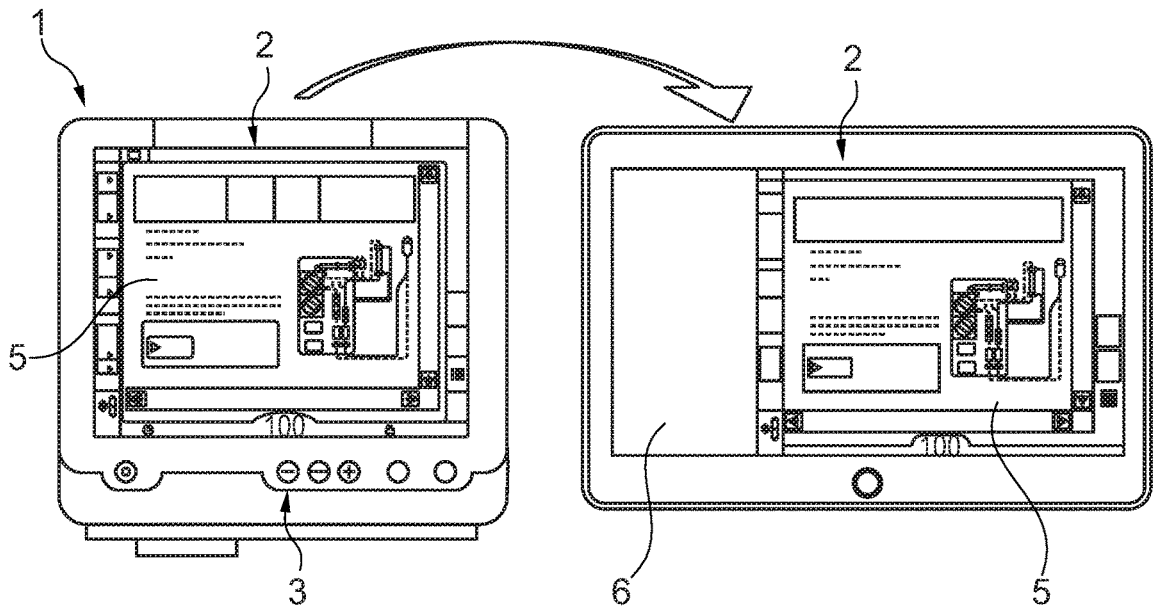
Fig. 1a
(Prior Art)
Fig. 1b
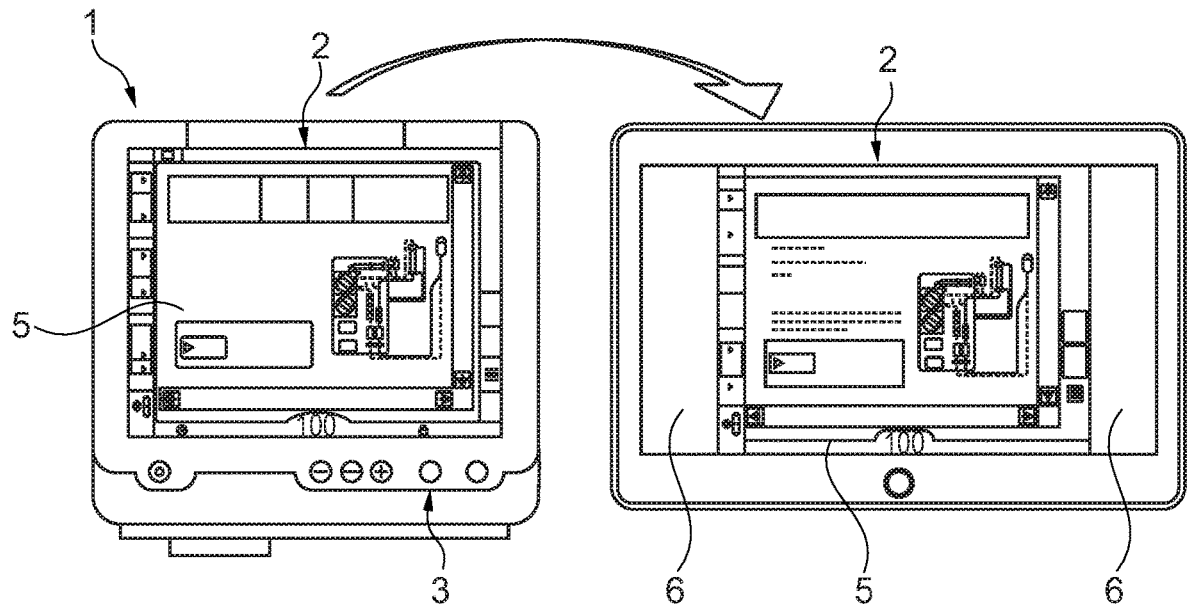
Fig. 2a
(Prior Art)
Fig. 2b

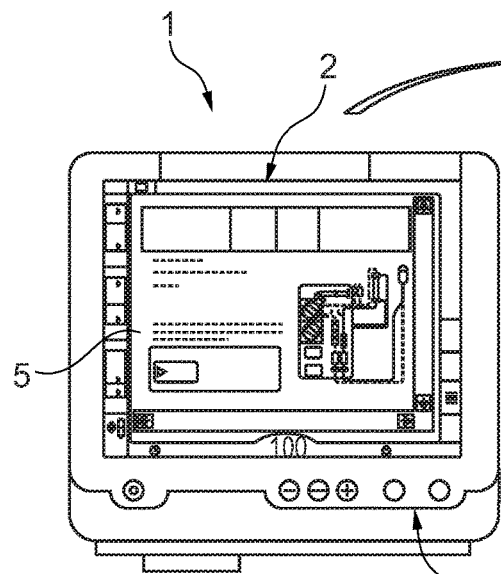
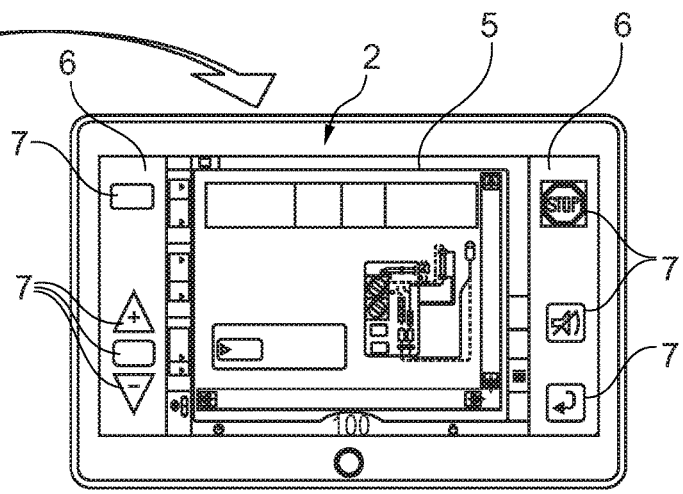
Fig. 3a (Prior Art)　　Fig. 3b
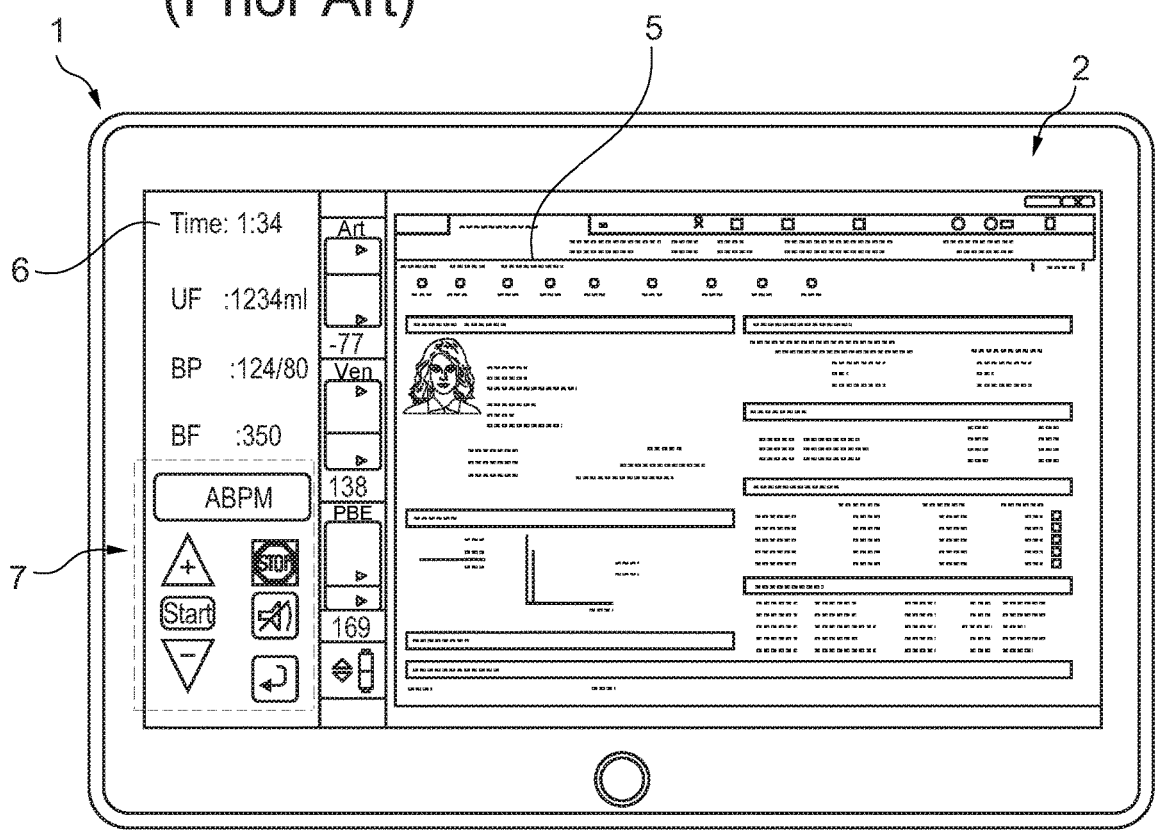
Fig. 4

DISPLAY APPARATUS OF A MEDICAL TREATMENT DEVICE

CROSS-REFERENCE TO RELATED APPLICATION(S)

This application is the United States national phase entry of International Application No. PCT/EP2019/073861, filed Sep. 6, 2019, and claims the benefit of priority of German Application No. 10 2018 122 035.9, filed Sep. 10, 2018. The contents of International Application No. PCT/EP2019/073861 and German Application No. 10 2018 122 035.9 are incorporated by reference herein in their entireties.

FIELD

The present disclosure relates to a display device of a medical treatment apparatus, especially a dialysis machine for displaying various parameters at least containing a set or a quantity of preferably patient-related treatment parameters and a set or a quantity of preferably clinic-related CIS parameters.

BACKGROUND

It is known from prior art that during treatment, especially during a dialysis treatment, users have to resort to a clinical information system. The clinical information system (in English abbreviated CIS), hereinafter referred to as "CIS", is understood to be a computer-aided system which serves for detecting, storing, manipulating and providing clinical information that is important to the health care process. A CIS may be limited to one single field such as e.g. a dialysis system, laboratory system etc. or may be more wide-spread and comprise practically all aspects of clinical information such as e.g. electronic medical records. Accordingly, the CIS offers a clinical data memory which collects, stores and administers information about the patient ranging from his/her personal data such as name, age, address and sex to all aspects of the treatment by the hospital. Moreover, the users may utilize tools by which appropriate information can be detected, manipulated, applied and displayed so that correct, prompt and evidence-based clinical decisions can be taken. In other words, the CIS represents a central collection of different information for patient care at spread locations.

Moreover, it is known from prior art that for access to the CIS during dialysis treatment a "COW" (computer on wheels) is provided. The COW is a "Thin Client" separate from the dialysis machine and flexibly movable which has enabled the CIS to be accessed so far. A Thin Client is understood to be a computer or a program that requires assistance by a server to be capable of fulfilling its tasks. In prior art, the Thin Client is connected to the CIS server so as to access and update data and information of the CIS during treatment via the COW. However, it is a drawback of this solution that the COW is an additional external apparatus which, in addition to the dialysis machine, requires space and is used for two patient beds. The latter aspect entails mainly concerns relating to hygiene.

It is further known from prior art that the Thin Client may be integrated in the dialysis machine. One example hereof is a system by Fresenius marketed under the trademark or tradename 2008T CDX™. The FMC CDX SYSTEM™ (Fresenius Medical Care Clinical Data Exchange) is a small computer which is incorporated in the dialysis machine and allows the users such as the caregivers or physicians to access the information system from any dialysis place. Thus, all information entered is immediately detected and uploaded into the information system without the user having to leave the dialysis area to change to a central computer.

Here the system has exactly one display which is integrated in the dialysis machine and a so-called CDX key which is adapted to switch between a treatment screen and the screen for displaying the CIS. It is a drawback in this case that the Fresenius CDX solution can display either only a set of patient-related treatment parameters or only a set of clinic-related CIS parameters on the display of the dialysis machine and between said two display configurations it can be switched only by means of an extra key on the input unit/operating unit. In the following, the two display configurations are referred to as treatment configuration and CIS configuration.

Moreover, practically all superior dialysis machines currently on the market have a 15" monitor with a 4:3 aspect ratio. The graphical user interface is geared to said format of the displays of the dialysis machines.

SUMMARY

Therefore, the object underlying the invention is to provide a display device of a dialysis machine which allows both simple operability and clear representation of various parameters on a display and enables CIS to be used along with a dialysis machine without any additional external devices.

The general idea underlying the invention is to provide exactly one display which is integrated in the dialysis machine and includes at least one input unit adapted to individually modify at least a set or a quantity of preferably patient-related treatment parameters and a set or a quantity of preferably clinic-related CIS parameters.

A set or a quantity of preferably patient-related treatment parameters are understood to be current values of the patient that are being continuously recorded and shown on the display, such as blood flow, blood pressure, dialysis fluid, ultrafiltration, limit values, heparin, time lapsed etc. The set or the quantity of preferably clinic-related parameters corresponds to the afore-mentioned explanation in prior art.

According to the underlying general idea, switching between the set or quantity of preferably patient-related treatment parameters and the set or quantity of preferably clinic-related CIS parameters is intended to be easily operated and to be possible without a shift key provided just for this purpose on a keyboard. Moreover, both the set or the quantity of preferably patient-related treatment parameters and the set or the quantity of preferably clinic-related CIS parameters are intended to be shown simultaneously on a display, when needed.

In detail, the display device of a dialysis machine for displaying various parameters includes exactly one display having a display area virtually divided into two display panels, the first display panel of which has large dimensions and the second display panel of which has small dimensions and includes at least two pre-set display configurations which can preferably be switched via the input unit, concerning a treatment configuration in which the set or the quantity of preferably patient-related treatment parameters is displayed exclusively in the first display panel and the set or the quantity of preferably clinic-related CIS parameters is displayed exclusively in the second display panel, and concerning a CIS configuration in which the set or the quantity of preferably patient-related treatment parameters is displayed exclusively in the second display panel and the set or the quantity of preferably clinic-related CIS parameters is displayed exclusively in the first display panel.

It is preferred in this context when the first display panel has a 4:3 aspect ratio. This is based on the fact that the dialysis machines currently on the market are configured with a graphical user interface (hereinafter referred to as GUI) corresponding to said aspect ratio as afore-described. When the aspect and/or size ratio is maintained, the effort of modifications on the graphical user interface for the first display panel is considerably minimized and the implementation can be realized with little effort as the 4:3 GUI can be continued to be used. This side-length ratio of the first display panel corresponds to the pre-set configuration for both display configurations.

The user may deviate from said pre-set configuration by dynamically varying the size of the first display panel manually by drawing the boundary between the first and the second display panel by the finger. Such variation is possible until the ratio of the first display panel to the second display panel is 50:50, for example. It depends on the information to be displayed which ratio will be set.

It is further advantageous when the display is in the form of a touchscreen and the input unit may be operated by touching the display. Alternatively, also a keyboard alone or in combination with a computer mouse or in combination with a touchscreen or a combination of all three input units is imaginable. In this way, switching between the two pre-set display configurations is possible by simple touching. Necessary inputs or adaptations of values, for example, are made preferably directly on the display, thus saving a separate keyboard which in turn requires space. A virtual keyboard may be automatically or manually overlaid on the screen, where needed.

In the CIS configuration, viz. when the set or the quantity of preferably patient-related treatment parameters is shown in the second display panel and the set or the quantity of preferably clinic-related CIS parameters is shown in the first display panel, the preferably patient-related treatment parameters are preferred to be reduced to the most important parameters such as e.g. the time lapsed, the blood pressure and the filtration.

The first display panel is preferred to be prioritized on the display area and to be manually shifted preferably via the input unit while the second display panel is automatically displaced or split. Thus, the first display panel can be displayed in the middle of the display. In this case, the second display panel is split into two parts. A respective part then is located on each side of the first display panel. The first display panel is always in the fore and is neither split nor concealed completely or partially. As an alternative, the first display panel may be disposed at the edge of the display. In this case, the entire second display panel is located either on the left or on the right of the first display panel.

By using the input unit in the form of a touchscreen according to the foregoing description, the first display panel may be positioned freely on the display by touching and correspondingly drawing said first display panel.

It is of further advantage when in the treatment configuration the set or the quantity of preferably clinic-related CIS parameters is shown in the second display panel in a sub-frame mode whose proportion to the area of the second display panel is especially automatically adapted in a preferably variable manner such that the side-length ratio thereof remains unchanged irrespective of the representation thereof in the first or second display panel. In other words, this means that the area of the second display panel occupied by the set or quantity of preferably clinic-related CIS parameters is adapted to the positioning of the first display panel in the treatment configuration. The type sizes are appropriately scaled, but do not go below a minimum font size required for readability.

In detail, this means that, when the first display panel is arranged on one side of the display, the addition of the horizontal length of the first display panel and of the horizontal length of the second display panel results in the horizontal total length of the display. In this context, the side-length ratio of the set or quantity of preferably clinic-related CIS parameters is maintained at 4:3 corresponding to the first display panel. Merely the size is varied. When the first display panel is arranged in the middle of the display, the set or the quantity of preferably clinic-related CIS parameters is displayed either on the right side or on the left side. Accordingly, in turn only the size but not the side-length ratio of the area occupied by the set or quantity of preferably clinic-related CIS parameters is varied. The horizontal length of said occupied area corresponds to the horizontal length of the second split display panel in which the set or quantity of preferably clinic-related CIS parameters is shown. The representation of the set or quantity of preferably clinic-related CIS parameters will be referred to as minimized window in the following.

Analogously, the invention is also applicable to a 16:9 display placed on edge, with the windows then being superimposed instead of being juxtaposed.

Of preference, in the treatment configuration the set or quantity of preferably clinic-related CIS parameters has been shown in the second display panel in the sub-frame mode only when the preferably clinic-related CIS parameters are processed/stored/updated. The time at which the preferably clinic-related CIS parameters are treated/processed/stored/updated will be referred to as CIS session in the following. After the set or quantity of preferably clinic-related CIS parameters in the CIS configuration has been treated or updated by a user during a CIS session and the user changes to the treatment configuration before the CIS session is completely terminated/concluded, the set or quantity of preferably clinic-related CIS parameters is continued to be shown in the second display panel. This is done as long as the CIS session is run in the background to process/store/update data. As long as the CIS session is active, switching to the CIS configuration is possible by touching the minimized window which is in the sub-frame mode. Thus, the minimized window of the CIS session serves as an icon.

It is advantageous when both in the treatment configuration and in the CIS configuration in the second display panel at least one button serving as an input unit is provided. The arrangement of the at least one button depends on the positioning of the first display panel on the display. This means that the at least one button spreads in the second display panel corresponding to the position of the first display panel. Depending on which of the two available display configurations is shown in the display, the arrangement of the at least one button adapts preferably automatically. This is to say that in the CIS configuration both the at least one button and the data reduced to the most important treatment parameters, as afore-described, are accommodated in the second display panel. This is applicable mutatis mutandis in the treatment configuration to the display of the active CIS session in the minimized window and the at least one button.

A button may be configured in different shapes/symbols and different functions may be assigned thereto. It is preferred when in the second display panel a button for starting and, resp., stopping the treatment, buttons for manually increasing and, resp., reducing values, preferably in the form of arrows, as well as a return button and a mute and sound button are provided. Further, an emergency button may be provided for simultaneously placing plural parameters in an area preferred in the case of emergency.

Preferably, the display of the display device for representing the first display panel and the second display panel has a total side-length ratio of 16:9. The use of a display having such side-length ratio offers the advantage that the general trend of the market not related to medical treatment apparatuses, especially dialysis machines, toward screens having a 16:9 format may be followed and thus no completely new screen formats have to be produced. This aspect in turn has a positive effect on the costs. When using a 16:9 screen in combination with a first display panel on the display according to the afore-described 4:3 aspect ratio, a residual area is remaining. Said residual area defines the second display panel. Analogously, displays having similar aspect ratios such as e.g. 20:10 may be used, of course.

Advantageously, a height resolution of the display is identical to a height resolution of the first display panel both in the treatment configuration and in the CIS configuration. This offers the advantage that the area of the first display panel corresponds to the otherwise customary 4:3 screen as to size and format and thus the already present GUI may be taken over. In this way, the same readability is ensured for the GUI without re-sampling/re-scanning the same.

Accordingly, the first display panel is preferred to be designed with 1024×768 pixels corresponding to a 4:3 aspect ratio and the second display is preferred to be designed with 768×342 pixels.

Moreover, the set or quantity of preferably clinic-related CIS parameters is preferred to be represented in the first display panel and/or in the second display panel by a process independent of the set or the quantity of preferably patient-related treatment parameters. Hence, the CIS session is preferably run in a browser window which shows the preferably clinic-related CIS parameters. Said independence of the two processes increases the safety of the apparatus and thus of the patient as well. If, for example, the CIS session crashes, the treatment may continue to be run without the patient's health being endangered. A different example relates to the situation that, if unauthorized persons/hackers access the CIS server, the treatment data cannot be directly accessed and finally manipulated, which might become dangerous to the patient's life.

According to another aspect of the invention, it is of advantage when the dialysis machine is designed to include a display device according to any one of the preceding aspects.

BRIEF DESCRIPTION OF THE DRAWING FIGURES

FIG. 1a is a schematic view of a known display device provided for comparison with FIG. 1b;

FIG. 1b is a schematic view of a first display panel on one side of a display in a treatment configuration according to the present disclosure;

FIG. 2a is a schematic view of a known display device provided for comparison with FIG. 2b;

FIG. 2b is a schematic view of the first display panel in the middle of the display in a treatment configuration according to the present disclosure;

FIG. 3a is a schematic view of a known display device provided for comparison with FIG. 3b;

FIG. 3b is a schematic view of the first display panel in the middle of the display in the treatment configuration including buttons according to the present disclosure;

FIG. 4 is a schematic view of the first display panel on one side of the display in a CIS configuration according to the present disclosure;

DETAILED DESCRIPTION

Figure 5:
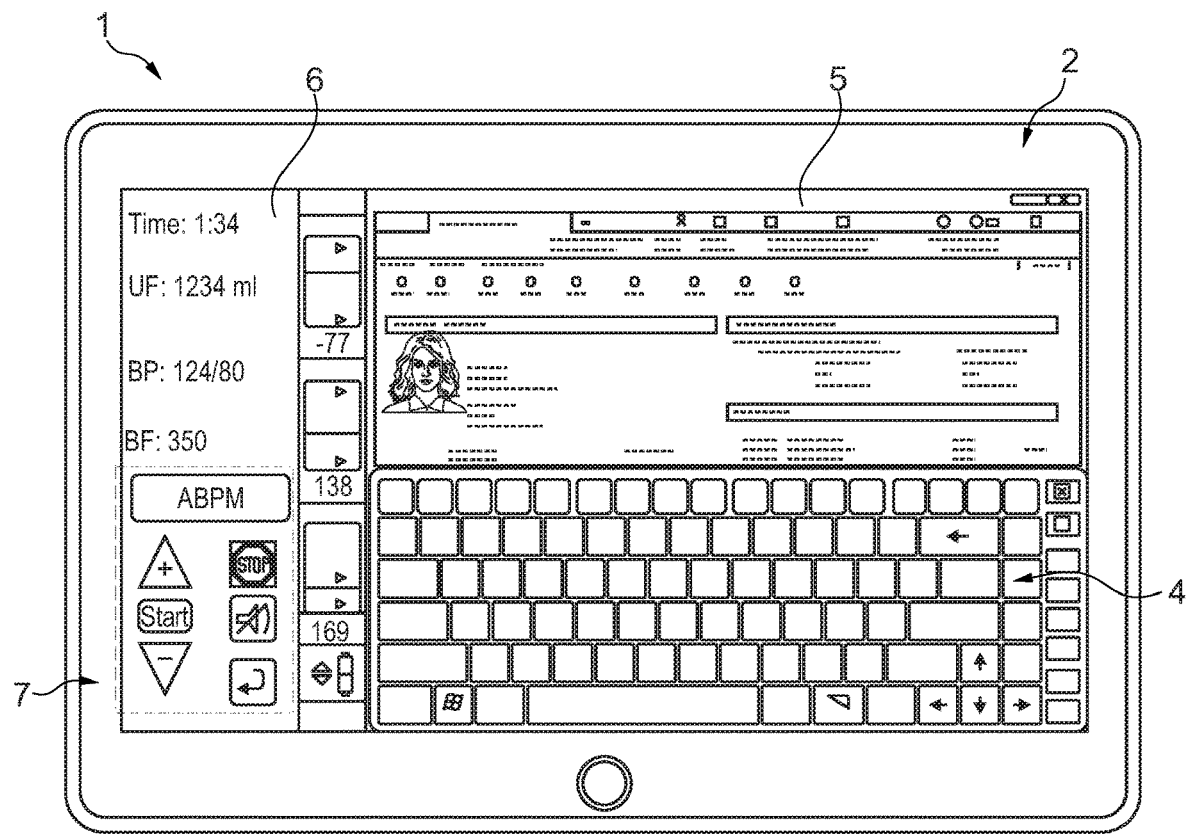
FIG. 5 is a schematic view of the first display panel on one side of the display in the CIS configuration including an input unit according to the present disclosure.

In the following, example embodiments of the present disclosure are described on the basis of the related figures. Like or functionally equivalent features are provided with like reference numerals in the individual figures and are appropriately not repeatedly described.

In each of the FIGS. 1b, 2b and 3b the display device 1 of a dialysis machine for representing various parameters on a display 2 according to the present disclosure is depicted. In each of the FIGS. 1a, 2a and 3a a picture of the display device 1 comprising a display 2 known from prior art is shown.

The display device 1 in FIGS. 1a, 2a and 3a according to prior art shows a display 2 indicating the treatment data. In the lower strip of the display device 1 beneath the display 2 various control buttons 3 are depicted. The display device 1 shows in the display 2 exclusively one display panel 5 which outputs treatment data. A keyboard serving as input unit 4 is not depicted. The display 2 and, correspondingly, the display panel 5 have an aspect ratio of 4:3.

FIG. 1b shows a schematic view of a first display panel 5 on one side (the right side in this case) of a display 2 in a treatment configuration according to the present disclosure. The display 2 has an aspect ratio of 16:9. The display area of the display 2 is divided into first and second display panels 5 and 6. The first display panel 5 shows the set or the quantity of preferably patient-related treatment parameters. The remainder not occupied by the first display panel 5 forms the second display panel 6 and in this exemplary Figure is empty/black. The first display panel 5 is configured to have a side-length ratio of 4:3 on the right side of the display 2. Alternatively, the first display panel 5 may as well be shown on the left side of the display 2. In this case, the second display panel 5 is shifted from the left side, as shown, to the right side.

FIG. 2b illustrates a schematic view of the first display panel 5 in the middle of the display 2 in the treatment configuration according to the present disclosure with a comparison to the prior art according to the foregoing description. In the exemplary configuration, the first display panel 5 further has an aspect ratio of 4:3 and the second display panel 6 is spread to the remaining display area of the display 2 not occupied by the first display panel 5. In contrast to FIG. 1, now two second display areas 6 are provided. The first display panel 5 again shows the set or the quantity of preferably patient-related treatment parameters and the two second display panels 6 are shown to be empty/black.

FIG. 3b is a schematic view of the first display panel 5 in the middle of the display 2 in the treatment configuration including buttons 7 according to the present disclosure with a comparison to the prior art shown in FIG. 3a as described in the foregoing. FIG. 3b illustrates the first display panel 5 and the second split display panel 6 on the right as well as on the left of the first display panel 5. In contrast to FIG. 2b, the second display panel is configured to have buttons 7. In FIG. 3b, in the second display panel 6 on the left side of the display 2 an activatable automatic blood pressure monitoring shown as ABPM, arrow keys including plus and minus for setting manually variable values and a stop key between the two arrow keys are exemplified as a button 7. In the second display panel 6 which is disposed on the right side of the display 2 a stop symbol, a return key as well as a loudspeaker symbol are exemplified. The arrangement of the buttons 7 is neither restricted to the arrangement shown here nor to the shown types of buttons 7. For example, all buttons 7 may as well be arranged in one half of the second display panel 6.

FIG. 4 illustrates a schematic view of the first display panel 5 on one side of the display 2 in a CIS configuration according to the present disclosure. In the display device 1 the first display panel 5 shows the set or the quantity of preferably clinic-related CIS parameters in a window/browser window independent of the set or the quantity of preferably patient-related treatment parameters.

On the left side of the display 2 in the second display panel 6, the set or the quantity of preferably patient-related treatment parameters is shown which are reduced to the most important treatment parameters such as the time, the ultrafiltration (in FIGS. 4 and 5 referred to as "UF"), the blood pressure (in FIGS. 4 and 5 referred to as "BP") and the blood flow (in FIGS. 4 and 5 referred to as "BF"). Moreover, in the exemplary view, the level in the arterial expansion chamber (referred to as "Art" in FIG. 4) and the level in the venous expansion chamber (referred to as "Ven" in FIG. 4) as well as the blood-side inlet pressure at the dialysis machine (referred to as "PBE" in FIG. 4) are permanently displayed. Alternatively, it is possible to manually exchange the selection of the prioritized patient-related treatment parameters pre-set in the CIS configuration.

Beneath the set or the quantity of preferably patient-related treatment parameters the buttons 7 are arranged. In contrast to the arrangement of the buttons 7 according to FIG. 3b, in FIG. 4 they are arranged in a compressed form in the second display panel 6. In the CIS configuration, the user may access the CIS server from the dialysis machine and may input/adapt/modify or have output data and, at the same time, observe the continuous patient-related treatment parameters. The user may switch to the treatment configuration by touching the display 2 in the second display panel 6 in the area of the treatment parameters.

FIG. 5 illustrates a schematic view of the first display panel 5 on one side of the display 2 in the CIS configuration including an input unit 4 according to the present disclosure. In the CIS configuration, preferably the input unit 4 is provided to be a keyboard, preferably in the lower half of the display 2 within the first display panel 5, which is operated by touching the touchscreen. Via said input unit 4 the preferably clinic-related CIS parameters are modified/adapted by the user. When the user has completed the input via the input unit 4 and switches to the treatment configuration, the window/browser window for showing the active CIS session is shown in a minimized window 8 in the second display panel 6 as long as the CIS session continues being active in the background to store/process data/modifications/inputs, as shown in FIG. 6.

Figure 6:
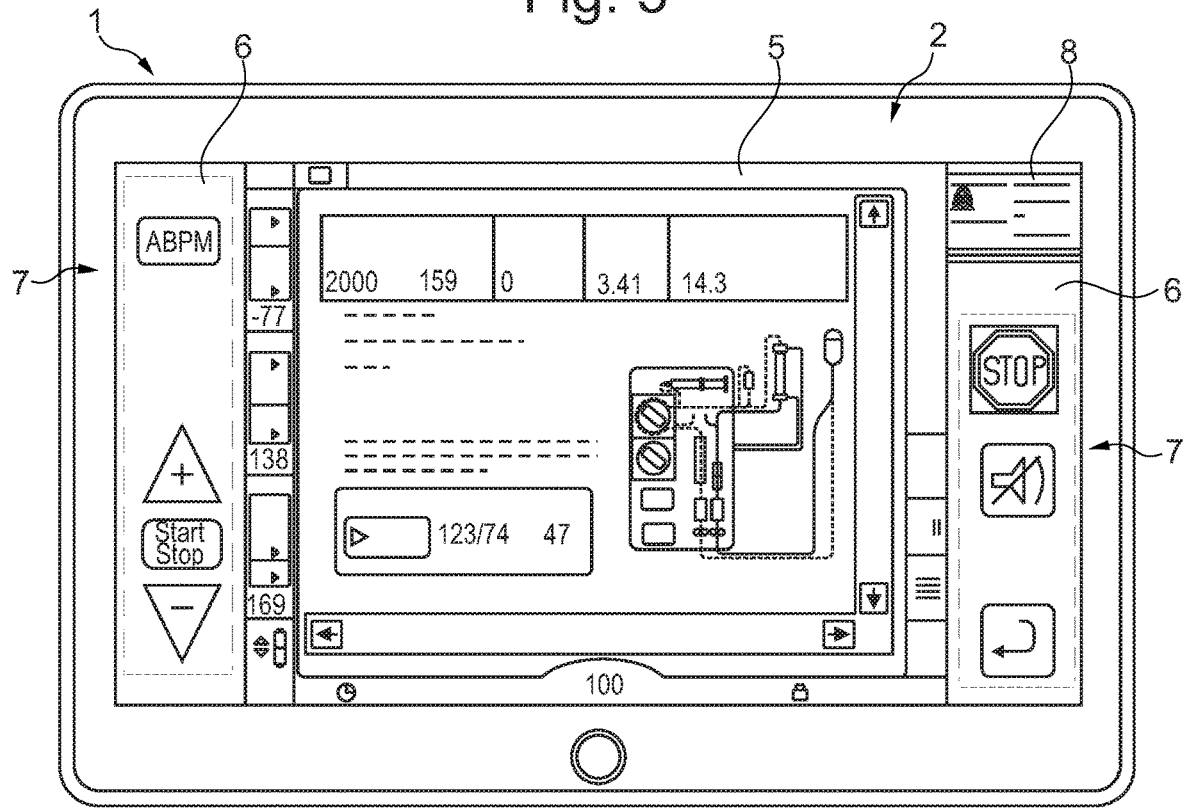
FIG. 6 is a schematic view of the first display panel in the middle of the display in the treatment configuration and an active CIS session according to the present disclosure.

FIG. 6 illustrates a schematic view of the first display panel 5 in the middle of the display 2 in the treatment configuration and an active CIS session according to the present disclosure. The minimized window 8 for showing the active CIS session in the background, while the system is in the treatment configuration, corresponds to the shown window in the first display panel 5 according to FIG. 5 for displaying the set or the quantity of preferably clinic-related CIS parameters in a minimized form. While the active CIS session is run in the background, the user has the option to return to the CIS configuration by touching the minimized window 8 which serves as icon. Preferably, the minimized window 8 maintains the side-length ratio of the first display panel 5 in the 4:3 format. Optionally, the size and the format may be dynamically adapted by drawing the boundaries by the fingers.

It is understood that the afore-described example embodiments and drawings that are not true-to-scale are merely of an exemplary nature and, in this respect, modifications may easily result for those skilled in the art without departing from the scope of the description. Nor are any external shapes, dimensions and the like subject to any particular limitations as long as they are provided and achieved by the effect and the functionality according to the invention.

The invention claimed is:

1. A display device of a medical treatment apparatus for displaying various parameters at least containing a quantity of patient-related treatment parameters and a quantity of clinic-related CIS parameters to a user, the display device comprising:
   exactly one display; and
   at least one input unit comprising at least one of a touchscreen, a keyboard, or a mouse, the at least one input unit adapted to individually modify at least the quantity of patient-related treatment parameters and the quantity of clinic-related CIS parameters,
   the exactly one display comprising a display area virtually divided into a first display panel and a second display panel, the first display panel having larger dimensions than the second display panel and the first display panel being prioritized on the display area with respect to the second display panel, the exactly one display switchable by the at least one input unit between at least two pre-set display configurations for the user, the at least two pre-set display configurations comprising: (1) a treatment configuration in which the quantity of patient-related treatment parameters is displayed exclusively in the first display panel and the quantity of clinic-related CIS parameters is displayed exclusively in the second display panel, and (2) a CIS configuration in which the quantity of patient-related treatment parameters is displayed exclusively in the second display panel and the quantity of clinic-related CIS parameters is displayed exclusively in the first display panel,
   the display of the quantity of clinic-related CIS parameters being carried out by a first process in at least one of the first display panel or in the second display panel and the display of the quantity of patient-related parameters being carried out by a second process in at least one of the first display panel or in the second display panel, where the first process is independent of the second process.

2. The display device according to claim 1, wherein the first display panel is manually displaceable by automatically displacing or splitting the second display panel.

3. The display device according to claim 1, wherein in the treatment configuration, the quantity of clinic-related CIS parameters is represented in the second display panel in a sub-frame mode in which a size ratio to an area of the second display panel is automatically adapted such that a side-length ratio thereof remains unchanged irrespective of a representation thereof in the first display panel or the second display panel.

4. The display device according to claim 3, wherein in the treatment configuration, the quantity of clinic-related CIS parameters is represented in the second display panel in the sub-frame mode only during a processing/saving/updating process of the quantity of clinic-related CIS parameters.

5. The display device according to claim 1, wherein at least one button is provided both in the treatment configuration and in the CIS configuration in the second display panel, the at least one button serving as an input unit.

6. The display device according to claim 5, wherein the at least one button spreads in the second display panel according to a position of the first display panel.

7. The display device according to claim 6, wherein an arrangement of the at least one button is automatically adapted in accordance with which of the at least two pre-set configurations is being presented to the one display.

8. The display device according to claim 1, wherein the display of the display device has a total side-length ratio of 16:9 for representing the first display panel and the second display panel.

9. The display device according to claim 8, wherein a height resolution of the exactly one display is identical to a height resolution of the first display panel both in the treatment configuration and in the CIS configuration.

10. The display device according to claim 1, wherein the first display panel is configured to have 1024×768 pixels and the second display panel is configured to have 768×342 pixels.

11. A dialysis machine comprising a display device according to claim 1.

12. The display device according to claim 1, wherein the at least one input unit comprises a touchscreen and a size and format of the first display panel is dynamically adjusted by drawing a boundary between the first display panel and the second display panel by the user's finger.

13. The display device according to claim 1, wherein the at least one input unit comprises a touchscreen and switching between the at least two pre-set display configurations comprises touching the touchscreen.

14. The display device according to claim 1, wherein the at least one input unit comprises a touchscreen and the first display panel is positioned freely on the one display by touching and drawing the first display panel on the touchscreen.

15. The display device according to claim 1, wherein the at least one input unit comprises a touchscreen and switching parameters displayed in the second display panel to the first display panel comprises touching the second display panel.

* * * * *